United States Patent [19]

Takahasi et al.

[11] Patent Number: 4,597,850

[45] Date of Patent: Jul. 1, 1986

[54] OXYGEN SENSOR

[75] Inventors: Toru Takahasi, Mito; Sadayasu Ueno, Katsuta, both of Japan

[73] Assignee: Hitachi, Ltd., Tokyo, Japan

[21] Appl. No.: 719,145

[22] Filed: Apr. 2, 1985

[30] Foreign Application Priority Data

Apr. 2, 1984 [JP] Japan .................................. 59-63369
Jun. 1, 1984 [JP] Japan ................................ 59-110770

[51] Int. Cl.$^4$ ...................... G01N 27/12; G01N 27/58
[52] U.S. Cl. ......................................... 204/426; 73/23; 338/34
[58] Field of Search ............... 204/428, 429, 425, 426, 204/1 S; 338/34; 73/23

[56] References Cited

U.S. PATENT DOCUMENTS

| T983,005 | 6/1979 | Akiyama et al. | 204/428 |
| 4,040,930 | 8/1977 | Dillon | 204/429 |
| 4,184,934 | 1/1980 | Bode et al. | 73/23 X |
| 4,199,423 | 4/1980 | Mann | 204/429 |
| 4,219,359 | 8/1980 | Miwa et al. | 204/428 X |
| 4,362,609 | 12/1982 | Sano et al. | 204/428 |
| 4,466,880 | 8/1984 | Torii et al. | 204/428 |

FOREIGN PATENT DOCUMENTS

| 2348505 | 4/1975 | Fed. Rep. of Germany | 204/428 |
| WO80/00373 | 7/1979 | PCT Int'l Appl. | |

Primary Examiner—G. L. Kaplan
Attorney, Agent, or Firm—Antonelli, Terry & Wands

[57] ABSTRACT

An oxygen sensor for monitoring the oxygen concentration in exhaust gases of an engine of a motor vehicle including a sensor element supported by a base in a position remote from the flow of exhaust gases to be tested whereby solid particles in the exhaust gases are prevented from being deposited on the sensor element and the sensor element is impervious to influences exerted by the temperature and flow velocity of the flow of exhaust gases. The oxygen sensor is capable of stably monitoring the oxygen concentration in exhaust gases of an engine of a motor vehicle with a high degree of performance over a prolonged period of time.

8 Claims, 6 Drawing Figures

OXYGEN SENSOR

BACKGROUND OF THE INVENTION

Field of the Invention

This invention relates to oxygen sensors, and, more particularly, to an oxygen sensor suitable for use in monitoring the concentration of oxygen in gases containing minute solid particles, such as exhaust emissions of motor vehicles.

One type of an oxygen sensor known in the art is based on the principles of oxygen concentration cell or oxygen pump in solid electrolytes, such as zirconia. Another type known in the art uses the phenomenon of transmission of oxygen ions in metal oxides, such as titania. It is well known that these oxygen sensors of the prior art are temperature-dependent. Proposals have been made to provide improvements to these temperature-dependent oxygen sensors, with one such proposal disclosed, for example, in Japanese Laid Open Application No. 166252/83 including the provision of a heating element located close to the sensor element to minimize influences which might be exerted on the sensor by the temperature of gases to be tested.

In order to achieve improved fuel efficiency and engine performance while avoiding environmental pollution by exhaust emissions by effecting finer control of fuel-air mixtures supplied to the engine of an automotive vehicle, there has been a demand to widen the range of operation of the oxygen sensors of the type referred to hereinbefore from the so-called theoretical air-fuel ratio to the entire range of working air-fuel ratios, particularly to lean mixtures. To meet this demand, it is necessary that the sensor element be controlled at a higher temperature (at a constant value in the range between 300° C. and about 800° C. at which the point of theoretical air-fuel ratio is sensed), in view of the physical properties of its material. The exhaust pipe of an automotive vehicle in which the oxygen sensor is mounted shows great fluctuations in temperature between −50° and +800° C. and in the velocity of air currents between 0 and 100 m/sec. This makes it necessary to pass an electric current to the oxygen sensor to heat same nearly at all times. However, to achieve economy in fuel consumption, it would be necessary to minimize electric power used for the purpose of heating. This would make it necessary to minimize the thermal capacity of the sensor and adopt support means which could inhibit transfer of heat to a portion of the exhaust pipe in which the sensor is mounted. As a result, the sensor including a support member has generally become elongated in shape, and proposals have been made to use a sensor element of small volume which may be either plate-like, disc-like or film-like in form, as disclosed, for example, in Japanese Patent Application Laid-Open No. 42965/83.

On the other hand, as noted in Automotive Vehicle Technology, 1972, Vol. 26, No. 9, exhaust emissions contain solid particles of carbon, magnesium, silicon, phosphorus, sulfur, calcium, chromium, iron, zinc, lead, etc., existing in the form of grit produced by the combustion reaction between sucked air and fuel or lubricant and the sliding contact between engine cylinders and pistons and between suction or discharge valves and the valve seats, and these solid particles are known to be deposited on walls and other parts of the exhaust pipes. In these deposits, lead, zinc, iron, chromium and calcium, relatively heavy in weight, remain in a solid state without vaporizing even if they are heated to 800° C. Thus, these elements remain deposited on the surface of the sensor element even if the latter is heated to a temperature of 800° C., making it impossible for the sensor element to perform monitoring due to the fact that the bores on the surface of the element for diffusing gases are blocked by the deposits or the triphasic interface of an electrode is covered with them. It is known that the smaller the size of the sensor element, the greater the influences exerted by the solid particles on the results achieved by the sensor.

This invention has as its object the provision of an oxygen sensor capable of maintaining its capacity to monitor the concentration of oxygen at a desired level over a very long time even if it is installed in a gas flow which contains solid particles and shows great fluctuations in temperature and flow velocity.

To accomplish the aforesaid object, the invention provides an oxygen sensor capable of reducing or minimizing influences which might be directly exerted by the gas flow on the sensor element for monitoring the concentration of oxygen in the gas.

According to the invention, the sensor element is enclosed by double cylinders including an outer cylindrical member and an inner cylindrical member, wherein a gas flow, admitted to the interior of the outer cylindrical member through openings formed in the outer cylindrical member, impinges on an outer wall surface of the inner cylindrical member so that solid particles in the gas are deposited thereon, and the gas flow is admitted to the interior of the inner cylindrical member through openings formed in the inner cylindrical member in positions in which the gas flow is out of alignment with the sensor element, to thereby reduce the flow velocity of the gas flow in a vicinity of the sensor element and render the latter imprevious to the influences of the gas flow.

According to further features of the invention, the sensor element is housed in a protective metal member of substantially cylindrical configuration which is closed at the bottom and formed with openings to allow a gas flow to enter into and exit from the protective metal member in positions remote from the sensor element in the protective metal member, whereby the majority of the gas flow entering the protective metal member passes through the vicinity of the supporting portion of the sensor which is near the inner wall surface of a passage of the tested gases and direct influences which might be exerted on the sensor element by the gas flow can be reduced.

DETAILED DESCRIPTION

Preferred embodiments of the oxygen sensor in conformity with the invention will now be described by referring to the accompanying drawings.

Figure 1:
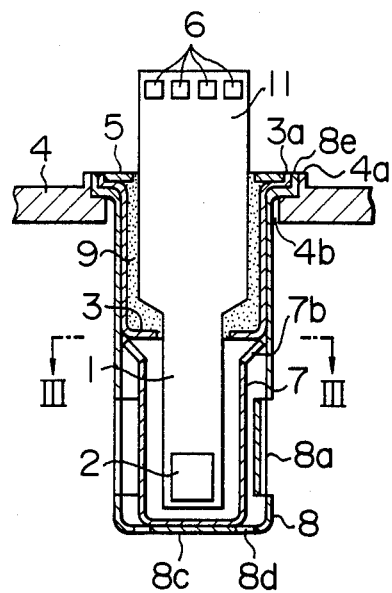
FIG. 1 is a vertical sectional view of the oxygen sensor comprising a first embodiment of the invention.
Figure 2:
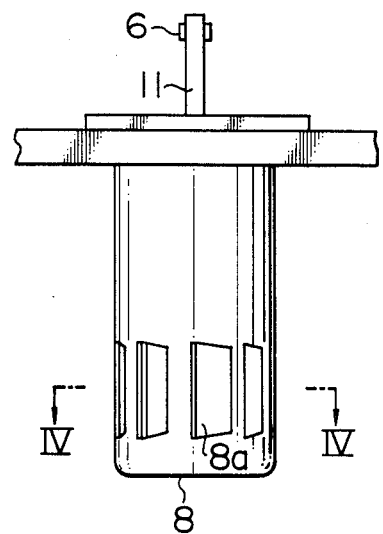
FIG. 2 is a side view of the oxygen sensor shown in FIG. 1.
Figure 3:
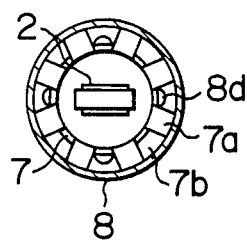
FIG. 3 is a transverse sectional view taken along the line III—III in FIG. 1.
Figure 4:
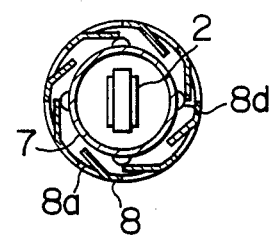
FIG. 4 is a transverse sectional view taken along the line IV—IV in FIG. 2.

Referring now to the drawings wherein like reference numerals are used throughout the various views to designate like parts and, more particularly, to FIG. 1, according to this figure the oxygen sensor comprises a base 1 of a rectangular plate shape having an increased width portion 11 serving as a partially-stabilized zirconium solid electrolyte. The base 1 supports, at its lower end portion, a sensor element 2 having a built-in electrical-heating element serving concurrently as a temperature-responsive element, and, at its upper end, conductive terminals 6 for the sensor element 2 and electrically-heating element which are connected to a control circuit, not shown. The base 1 is supported by a support metal member 3 of substantially cylindrical configuration formed with slots and closed at its bottom in such a manner that the conductive terminals 6, located at the increased width portion 11, stick out the support metal member 3, with an airtight sealing member 9, such as aluminum oxide powder, talc powder or an inorganic adhesive agent filling a gap between the base 1 and the support metal member 3 to firmly secure the former to the latter.

The oxygen sensor comprises an outer metal member 8 which is of substantially cylindrical configuration and closed at its bottom and which is formed at its peripheral wall with eight louvered slots 8a and at its bottom with four circular openings 8d. The oxygen sensor comprises an inner metal member 7, substantially cylindrical in configuration, closed at its bottom and spread outwardly at its open top end portion which is formed with eight claws 7a and eight cutouts 7b arranged in the form of a rosette, which is inserted in the outer metal member 8 and joined at its bottom to a bottom wall 8c of the outer metal member 8 by spot welding. When the inner metal member 7 is fitted in the outer metal member 8, the cutouts 7b and the louvered slots 8a are out of alignment with each other as viewed in a longitudinal direction of the sensor as shown in FIG. 1, and the claws 7a are maintained at their outer edges in contact with an inner surface of the peripheral wall of the outer metal member 8 while the circular openings 8d are not closed by the bottom of the inner metal member 7. The outer metal member 8 is spread outwardly at its open top end portion to provide a flange 8e which is fitted to a stepped circular edge portion 4a of a mounting metal member 4 after the cylindrical outer metal member 8 is inserted in a circular opening 4b of the mounting metal member 4. A flange 3a of the support metal member 3 is fitted in the flange 8e, and a disc-shaped lid 5 formed with slots is fitted in the flange 3a and joined by welding at its entire circumference to an inner surface of the flange 3a to provide the oxygen sensor which, in its completed form, is mounted to the mounting metal member 4. After the oxygen sensor is thus completed, the sensor element 2 of the oxygen sensor is located in such a manner that it is out of alignment with the cutouts 7b formed in the inner metal member 7 lengthwise of the oxygen sensor as shown in FIG. 1.

The oxygen sensor of the invention described hereinabove is fitted to an exhaust pipe, not shown, of an engine of a motor vehicle by the mounting metal member 4. As the conductive terminals 6 are connected to the power source of the control circuit and the louvered slots 8a are exposed to a flow of exhaust gas in and through the exhaust pipe, the exhaust gases find their way into the outer metal member 8 through the louvered slots 8a, and main currents of gas flow in vertical movement between the inner and outer metal members 7, 8 before being released to outside through the louvered slots 8a. A portion of the gas flowing into the outer metal member 8 flows in two directions longitudinally of the oxygen sensor, namely, the gas flowing in one direction flows out of the circular openings 8d at the bottom of the outer metal member 8, and the gas flowing in the other direction flows through the cutouts 7b into the inner metal member 7 and the majority of gases flows out of the inner metal member 7 into the outer metal member 8.

Accordingly, the solid particles contained in the currents of exhaust gases, particularly those which are heavy in weight, are blocked in their flow by the outer wall surface of the outer metal member 8, and trapped between the outer wall surface of the inner metal member 7 and the inner wall surface of the outer metal member 8 while only those solid particles which are light in weight find their way into the inner metal member 7 through the cutouts 7b and nearly all of them flow out of the inner metal member 7 into the outer metal member 8 through the cutouts 7b. Thus, almost no solid particles are brought into contact with the sensor element 2 remote from the cutouts 7b, with only a portion of the particles, very light in weight, such as carbon which is flammable, swirling in the inner metal member 7. Since the sensor element 2 is maintained at a high temperature of 800° C. by the builtin electrical-heating element, the swirling solid particles are combusted and not allowed to be deposited on the sensor. The circular openings 8d at the bottom of the outer metal member 8 serve the purpose of releasing to outside from the outer metal member 8 the solid particles which impinge on the outer wall surface of the inner metal member 7 and the inner wall surface of the outer metal member 8.

In the embodiment of the oxygen sensor of the construction described hereinabove, it is possible to advantageously avoid fluctuations in temperature to which the sensor element 2 might be exposed. More specifically, the outer metal member 8 has the effect of reducing changes in the temperature of exhaust gases flowing through the exhaust pipe, and the gases flowing through the louvered slots 8a into the outer metal member 8 have changes in temperature reduced by the inner metal member 7. The difficulty with which the energy of the exhaust gases imparted to the inner metal member 7 is transferred to the support metal member 3 of low temperature further reduces changes in the temperature of the exhaust gases. Thus, the changes in temperature to which the sensor element 2 disposed in the lower portion of the inner metal member 7 is exposed can be greatly reduced.

The embodiment of the oxygen sensor of the aforesaid construction is also capable of avoiding fluctuations in the flow velocity of exhaust gases to which the sensor element 2 is exposed. More specifically, as the flow velocity increases, the flow of exhaust gases admitted to the outer metal member 8 through the louvered slots 8a swirls by the louvers and is released to outside through the louvered slots 8a after moving peripherally in the outer metal member 8 at increased flow velocity, and the flow of exhaust gases in the outer metal member 8, oriented longitudinally in two directions, is not appreciably accelerated. Thus, the flow velocity of gases admitted to the inner metal member 7 through the cutouts 7b, much less that of gases flowing in the vicinity of the sensor element 2, shows no great changes. It will be appreciated that, although the flow velocity of exhaust gases flowing outside the outer metal member 8 shows great fluctuations, the flow velocity of exhaust gases in the vicinity of the sensor element 2 is not greatly affected by the fluctuations in the flow velocity of exhaust gases outside the outer metal member 8 and remains substantially constant at all times.

In the embodiment shown in FIGS. 1-4, the open end portion of the cylindrical inner metal member 7 closed at the bottom is spread outwardly and the cutouts 7b, serving as gas ports, are formed in the outwardly spread open end portion of the member 7. However, this is not restrictive, and cutouts may be formed without outwardly spreading the open end portion of the member 7. Also, the inner metal member 7 need not be cylindrical in form so long as it is closed at the bottom and open at the top, and the invention is not limited to the specific shape and number of the cutouts 7b. What is important is that the gas ports be formed in positions in which they do not face the sensor element 2 and the flow velocity of gases be made relatively lower in positions near the sensor element 2 than in positions remote from the sensor element 2.

In the embodiment of the oxygen sensor shown in FIGS. 1-4, the outer metal member 8 of substantially cylindrical configuration closed at its bottom is formed with eight louvered slots 8a at its peripheral wall and four circular openings 8d at its bottom. However, the outer metal member 8 may be cylindrical in configuration without a closed bottom, and may be formed at its peripheral wall with openings other than the louvered slots. The outer metal member 8 may be formed at its bottom with openings which are not circular in shape, and the openings at the bottom may be dispensed with or the bottom may be open without being closed. What is important is that the gas ports formed in the outer metal member 8 be not essentially aligned with the gas ports formed in the inner metal member. This arrangement of the gas ports in the outer and inner metal members is covered by the scope of the invention.

Figure 6:
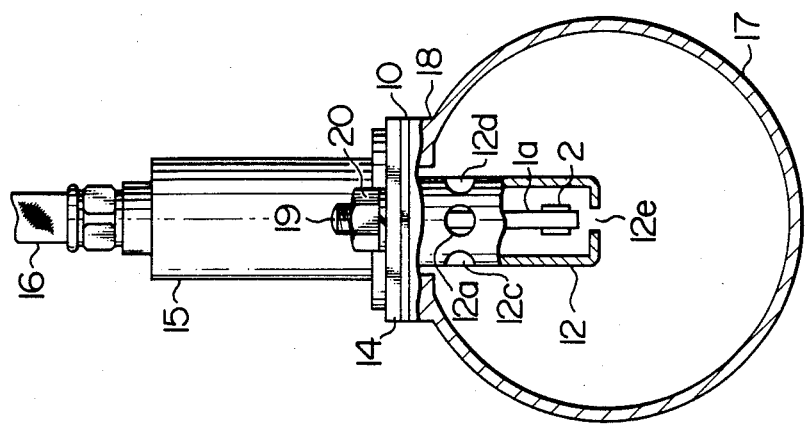
FIG. 6 is a fragmentary vertical sectional view of the oxygen sensor similar to that shown in FIG. 5 but shown in a cross section perpendicular to the base of the sensor.
Figure 5:
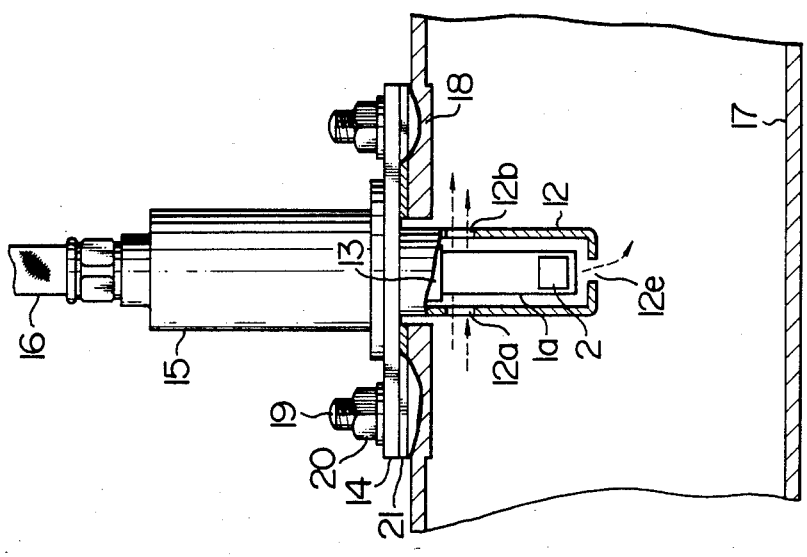
FIG. 5 is a fragmentary vertical sectional view of the oxygen sensor comprising a second embodiment of the invention, shown in a cross section which is parallel to the base of the sensor.

In FIGS. 5 and 6, the oxygen sensor comprises a base 1a of substantially rectangular plate-like configuration formed of the same electrolyte as the base 1 of the first embodiment, and the sensor element 2 is mounted at one end portion of the base 1a which supports at an opposite end portion wires for electrically connecting the sensor element 2 and heating element with a harness 16. The base 1a is supported at its intermediate portion by a support metal member 13 having a flange, and airtightly sealed as is the case with the base 1 of the first embodiment.

A protective metal member 12 of substantially tubular configuration is closed at its bottom and formed with a flange at an open end portion, with the protective metal member 12 being fitted in a stepped opening of a metal flange 14 and joined to the support metal member 13 by welding. An outer metal member 15 of substantially cylindrical configuration is formed with a flange at an open end of its major diameter portion which is fitted in the stepped opening of the metal flange 14 and joined thereto by welding. The outer metal member 15 is clamped at its minor diameter portion to support the harness 16. The protective metal member 12 is formed with gas ports 12a, 12b, 12c and 12d at its peripheral wall near the flange, and with a gas port 12e of a smaller diameter than the gas ports 12a-12d at its bottom wall near the sensor element 2. The parts described hereinabove constitute a main body of the oxygen sensor. A sensor mount 18 having stud bolts 19, is attached to an exhaust pipe 17 of the motor vehicle, and the main body of the oxygen sensor is mounted on the sensor mount 18 through a packing 21, and a nut 20 is threadably fitted to each stud bolt 19. When the main body of the oxygen sensor is fitted to the exhaust pipe 17 as described hereinabove, the gas ports 12a-12d of the protective member 12, formed at its peripheral wall, are located in the immediate vicinity of an inner wall surface of the exhaust pipe 17 and the sensor element 2 is located in a position remote from the gas ports 12a-12d at the peripheral wall of the protective metal member 12. When the exhaust gases flow from left to right in FIG. 5, the flow of exhaust gases through the exhaust pipe 17 is shed by the peripheral wall of the protective metal member 12 and a portion of the exhaust gases is admitted through the gas port 12a at the peripheral wall thereof. The major portion of the exhaust gases, admitted through the gas port 12a, is released to outside through the gas port 12b diametrically opposed to the gas port 12a while a small portion thereof is released to outside through the gas port 12e at the bottom of the protective metal member 12.

As described in the background of the invention, the temperature and flow velocity of exhaust gases flowing through the exhaust pipe show great fluctuations between 50° and 800° C. and between 0 and 100 m/sec., respectively, and the exhaust gases contain solid particles of metallic and non-metallic origin. In the embodiment shown in FIGS. 5 and 6, the exhaust gases flow through the protective metal member 12 in a position remote from the sensor element 2, so that the majority of the solid particles, particularly those of metallic elements of heavy weight, is released through the gas port 12b by the flow of exhaust gases of high velocity without impinging on the surface of the sensor element 2 and adhering thereto. Only a small portion of the solid particles, particularly those of light weight, such as carbon particles, may possibly be released through the gas port 12e at the bottom of the protective metal member 12. However, since the sensor element 2 is maintained at a high temperature of 800° C. by the heating element, the solid particles of light weight floating in the protective metal member 12 are prevented from being deposited on and adhering to the surface of the sensor element 2.

In the embodiment shown and described hereinabove, control of the temperature of the sensor element by means of the heating element is advantageously effected. More specifically, even if the temperature and flow velocity of exhaust gases flowing through the exhaust pipe 17 show great fluctuations, changes in the temperature and flow velocity of the exhaust gases in the protective metal member 12 are greatly reduced because the gas ports 12a-12d formed at the peripheral wall of the protective metal member 12 are located in the immediate vicinity of the inner wall surface of the exhaust pipe 17. Moreover, since the sensor element 2 is remote from the gas ports 12a-12d and the inner wall surface of the exhaust pipe 17, influences exerted on the sensor element 2 by the transfer of heat to and from the base 1a are greatly reduced.

In the foregoing description, the flow of exhaust gases has been described as being oriented in one direction. However, in actual practice, the direction of flow of exhaust gases might undergo a change when the motor vehicle suddenly accelerates or decelerates. In this case, if no other gas ports were provided than the gas ports 12a-12d formed at the peripheral wall of the protective metal member 12, the flow velocity of exhaust gases in the protective metal member 12 would fluctuate greatly due to a pumping action, and the exhaust gases would show a fluctuation in flow velocity to a considerable degree in the lower portion of the protective metal member 12 or in the vicinity of the sensor element 2, with a result that the output of the sensor element 2 might show a variation which has nothing to do with the concentration of oxygen and the solid particles might impinge on and adhere to the sensor element 2. However, the provision of the gas port 12e at the bottom wall of the protective metal member 12 in addition to the gas ports 12a-12d at the peripheral wall thereof has the effect of minimizing the pumping action occurring in the protective metal member 12, making it possible to prevent a change or a rise in the flow velocity of exhaust gases in the vicinity of the sensor element 2 and to keep solid particles from being deposited on the sensor element 2. The gas port 12e formed at the bottom wall is smaller in diameter than the gas ports 12a-12d formed at the peripheral wall. Combined with static pressure, this reduces the volume of exhaust gases flowing through the gas port 12e to a level below the volume of exhaust gases flowing through the gas ports 12a-12d in almost all the engine speed range of motor vehicles in which the flow velocity of exhaust gases is constant or shows a gradual reduction. What is essential is that the flow rate of exhaust gases through the gas port 12e formed at the bottom wall be substantially reduced to a level below the flow rate of exhaust gases through the gas ports 12a-12d formed at the peripheral wall.

In the foregoing description, the base of the oxygen sensor has been described as having a rectangular plate shape and being provided with a heating element. It is to be understood that the invention can also have application in an oxygen sensor including a base of a shape different from the one described and having no heating element, such as a base in the form of a square post or a column, so long as the sensor element is located in a position remote from the wall of a passage of exhaust gases to be tested. The invention has the effect of preventing solid particles from being deposited on the sensor element supported by the base of the aforesaid shape while avoiding changes in temperature which the sensor element might undergo.

When the oxygen sensor according to the invention is mounted in a position in which the flow of exhaust gases to be tested is constant in direction, the gas port 12e at the bottom wall or the gas ports 12c and 12d at the peripheral wall may be dispensed with.

The gas ports 12a-12d at the peripheral wall and the gas port 12e at the bottom wall are circular in shape. However, the invention is not limited to this specific shape of the gas ports, and the gas ports 12a-12e may be of any shape as desired, such as square or rectangular. The gas ports have been described as being two to five in number. However, the invention is not limited to these specific numbers. Any arrangement whereby a flow of exhaust gases through the protective metal member 12 is made essentially remote from the sensor element 2 and near the inner wall surface of the exhaust pipe 17 is covered by the scope of the claim for a patent in the subject application.

The second embodiment of the invention shown in FIGS. 5 and 6 enables a prevention of the deposition of solid particles in the exhaust gases on the sensor element to be avoided. Also, the influences exerted on the sensor element by fluctuations in the temperature and flow velocity of the exhaust gases monitored can be minimized. In addition, an error in the output of the sensor element which might be caused to occur by a change in the direction of flow of the exhaust gases monitored can be eliminated. Thus, the embodiment shown in FIGS. 5 and 6 is capable of performing the operation of monitoring the oxygen concentration in the exhaust gases stably over a prolonged period of time.

In the embodiments shown in FIGS. 1-6, the oxygen sensor has been described as including a sensor element supported by a base of zirconium solid electrolyte of rectangular plate shape and having a built-in electrically-heating element. It is to be understood that the invention can achieve similar effects when applied to oxygen sensors in which no built-in electrically-heating element is provided and the sensor element and conductive base supporting the sensor element are separate entities and in which the sensor element and base are separate entities and their shapes are not plate-like, so long as the sensor element is located in a position remote from the position in which the sensor is supported.

The present invention can achieve, in oxygen sensors including all the types of sensor elements for monitoring the concentration of oxygen, the following effects: first, solid particles in the exhaust gases tested can be prevented from being deposited on the sensor element; secondly, the sensor element is not influenced by fluctuations in the temperature of the exhaust gases tested; and thirdly, the sensor element is not influenced by changes in the flow velocity of the exhaust gases tested. These features enable the oxygen sensor according to the invention to perform, with a high degree of performance, the function of stably monitoring the concentration of oxygen in the exhaust gases of an engine of an automotive vehicle flowing through its exhaust pipe over a prolonged period of time.

What is claimed is:

1. An oxygen sensor of a double cylinder type, comprising:
   a sensor element;
   an inner cylindrical member formed with gas ports, said inner cylindrical member housing said sensor element and being closed at a bottom end thereof;
   an outer cylindrical member enclosing said inner cylindrical member, said outer cylindrical member being closed at a bottom end thereof;
   wherein said gas ports are formed at a peripheral wall of said inner cylindrical member in positions in which they are not in face-to-face relation to the sensor element; and
   wherein gas ports are formed at a peripheral wall of said outer cylindrical member in positions in which they are not in face-to-face relation to the gas ports formed at the peripheral wall of the inner cylindrical member.

2. An oxygen sensor as claimed in claim 1, wherein said gas ports formed at the peripheral wall of the outer cylindrical member are in the form of louvered slots.

3. An oxygen sensor as claimed in claim 4, wherein said outer cylindrical member is formed with gas ports at its bottom.

4. An oxygen sensor as claimed in claim 1, wherein said outer cylindrical member is closed at its bottom by a bottom wall formed with gas ports.

5. An oxygen sensor of a double cylinder type, comprising:
   a sensor element;
   an inner cylindrical member formed with gas ports, said inner cylindrical member housing said sensor element; and
   an outer cylindrical member enclosing said inner cylindrical memeber;
   wherein at least said inner cylindrical member is closed at its bottom and said gas ports are formed at a peripheral wall of said inner cylindrical member in positions in which they are not in face-to-face relation to said sensor element; and
   wherein said inner cylindrical member is formed with gas ports at its bottom.

6. An oxygen sensor as claimed in claim 5, wherein an open end portion of said inner cylindrical member is outwardly spread to provide an outwardly spread open end portion whereby the inner cylindrical member is maintained at the outwardly spread open end portion in contact with an inner surface of the peripheral wall of the outer cylindrical member and supported thereby.

7. An oxygen sensor as claimed in claim 5, wherein said inner cylindrical member is firmly secured at its bottom to the bottom of said outer cylindrical member and supported thereby.

8. An oxygen sensor as claimed in claim 5, wherein the gas ports formed at said inner cylindrical member are located at said outwardly spread open end portion of the inner cylindrical member.

* * * * *